United States Patent [19]

Vincek

[11] 4,295,566
[45] Oct. 20, 1981

[54] AIR-EVACUATED PACKAGE WITH VACUUM INTEGRITY INDICATOR MEANS

[75] Inventor: Robert C. Vincek, Clifton, N.J.

[73] Assignee: Becton, Dickinson and Company, Paramus, N.J.

[21] Appl. No.: 147,698

[22] Filed: May 7, 1980

[51] Int. Cl.³ .................. B65D 81/20; G01L 19/12
[52] U.S. Cl. .................................. 206/457; 73/49.2; 116/266; 116/270; 206/524.8
[58] Field of Search .................. 206/524.8, 216, 457, 206/361; 116/270, 266; 73/49.2

[56] References Cited

U.S. PATENT DOCUMENTS

| | | | |
|---|---|---|---|
| 2,821,951 | 2/1958 | Carver | 206/216 |
| 3,238,599 | 3/1966 | Bauman | 206/216 |
| 3,374,882 | 3/1968 | Amaliksen | 206/361 |
| 4,054,204 | 10/1977 | Keeton | 206/524.8 |

*Primary Examiner*—William T. Dixson, Jr.
*Attorney, Agent, or Firm*—Richard J. Rodrick

[57] ABSTRACT

An evacuated article-containing package assembly with a vacuum integrity indicator comprises an air-impervious package having an access opening and having at least a flexible portion. An article is included inside the package. A member is included inside the package which is compressible under the influence of pressure less than atmospheric pressure. A closure seal is on the package for sealing the access opening, with the sealed package being air-evacuated. The compressible member is adapted to expand against the flexible portion of the package to outwardly expand the flexible portion if the pressure inside the package equalizes with the pressure outside the package. When this occurs, the expanded flexible portion serves as a visual indicator that there is no vacuum condition inside the package.

9 Claims, 5 Drawing Figures

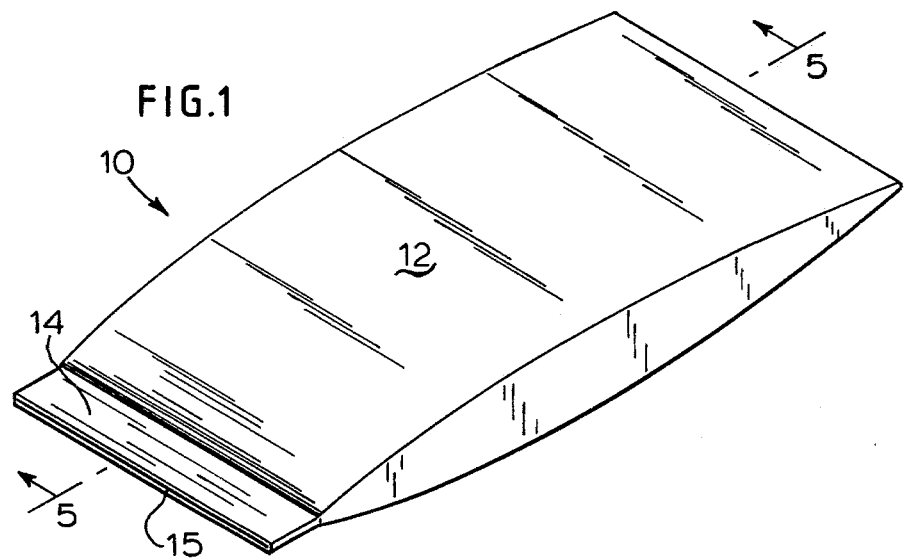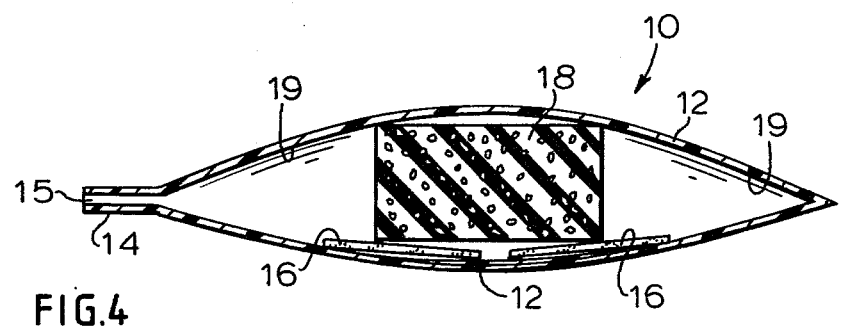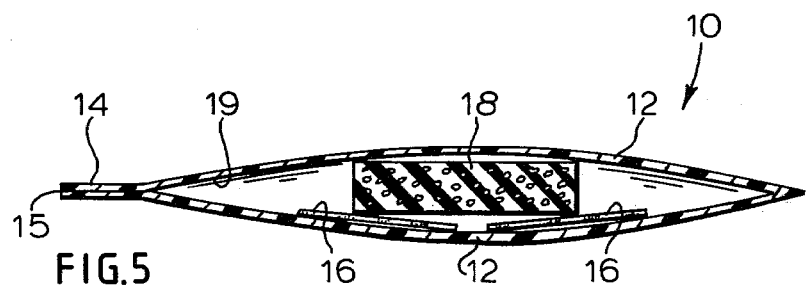

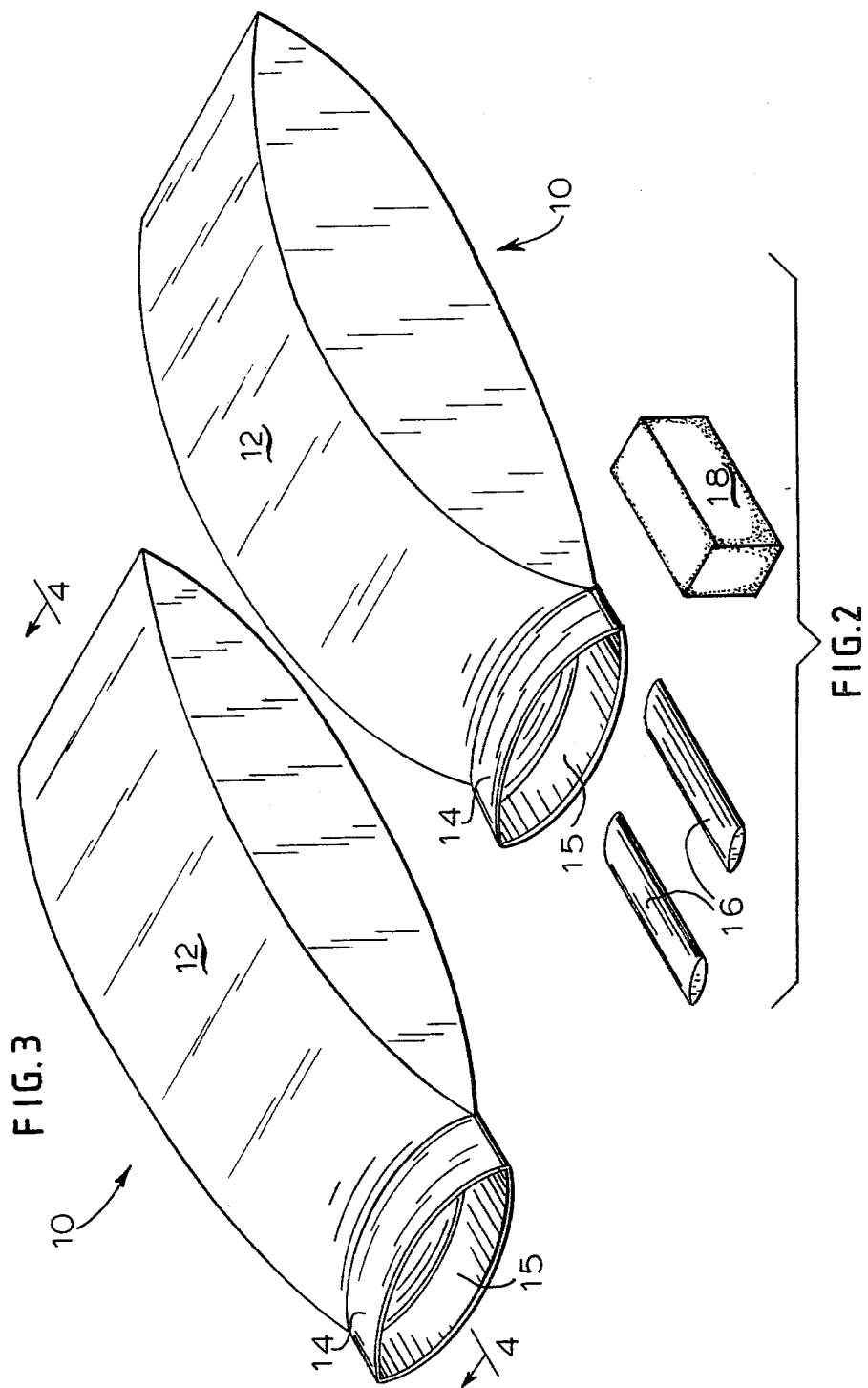

AIR-EVACUATED PACKAGE WITH VACUUM INTEGRITY INDICATOR MEANS

BACKGROUND OF THE INVENTION

The present invention generally relates to a sealed, air-evacuated, article-containing package, and more particularly, concerns such a package with a visual indicator for determining the integrity of the package to assure a vacuum condition.

Many sterile, clean or perishable articles are packaged in air-evacuated containers in order to preserve those characteristics just mentioned. In sealing such air-evacuated packages, there is always the possibility that a defect in the package will occur by which the vacuum condition inside the package will be lost. For example, package material or seal failure could occur which would cause the vacuum inside the package to be lost since the pressures both inside and outside the package would tend to equalize.

In many such packages, there is no easy way to tell, especially by visual checking, whether the desired vacuum condition inside the package is being maintained. Various types of somewhat cumbersome testing techniques are often employed with these packages to make such a determination. For instance, one such testing method requires the introduction of a pressurized gas into a randomly sampled package which is partially submerged in a sterile fluid. Another method relies only on the visual appearance of sampled packages, and an arbitrary decision is generally made as to whether or not a suitable vacuum is being maintained inside the package. It can be seen that this type of testing is clearly arbitrary and subjective, with reliability and accuracy notably lacking in these procedures.

With such deficiencies such as described above facing those who attempt to easily and readily determine whether vacuum conditions exist inside an air-evacuated package, it becomes apparent that there is a need for improvements in technique. It is to the solution of these deficiencies that the present invention is directed.

SUMMARY OF THE INVENTION

An evacuated article-containing package assembly with vacuum integrity indicator means comprises an air-impervious package having an access opening and at least a flexible portion thereof. An article is inside the package, and compressible means is included being compressible under the influence of pressure less than atmospheric pressure. Sealing means is on the package for sealing the access opening with the sealed package being air-evacuated. The compressible means is adapted to expand against the flexible portion of the package to thereby outwardly expand the flexible portion if the pressure inside the package is substantially equal to the pressure outside the package. This expanded flexible portion thereby serves as a visual indicator that there is no vacuum condition inside the package.

In the preferred embodiment of the present invention, the entire package is made of flexible material and the compressible means is preferably a high-density, open cell foam material. One example of such foam material is an open cell polyurethane.

A significant feature and advantage of the present invention lies in the visual determination concerning the vacuum condition inside the package. For example, a more flattened package is a clear indication that there is a vacuum inside the package; should the package be expanded or bloated in appearance, the user can quickly and easily make the determination that there is no vacuum inside the package. This feature then advantageously eliminates the requirement for the previously known and used testing techniques such as the injection of pressurized gas inside a submerged package, or arbitrary decision based on the package's visual appearance. Thus, this saves inspection time and materials which have been required to complete the previously used testing techniques. Of most significance is the accuracy of the present invention. Whereas the prior testing techniques relied heavily upon a subjective determination, the present invention relies principally upon the objective criteria of comparing sizes of packages or sizes of compressible means for the determination of vacuum conditions. The great disparity between the flattened-vacuum maintained package and the greatly expanded, non-vacuum package and size of compressible means makes it readily apparent which of the two conditions exist inside any such package. Furthermore, the ability to identify an intact package, which has had its vacuum compromised, assures a significantly higher quality control level, since such a defective package can be inspected more easily during different phases of manufacture and distribution. It will be perceived from a further reading of the present invention, that other advantages are offered as well.

BRIEF DESCRIPTION OF THE DRAWINGS

FIG. 1 is a perspective view of one embodiment of the present invention shown with the package in a sealed, air-evacuated condition;

FIG. 2 is a perspective view of one package of the present invention ready to receive articles therein along with the compressible member;

FIG. 3 is a perspective view of the package of FIG. 2 as it appears with the contents therein but no vacuum inside the package;

FIG. 4 is a cross-sectional view taken along line 4—4 of FIG. 3 illustrating the inside of the package when no vacuum conditions exist; and FIG. 5 is a cross-sectional view taken along line 5—5 of FIG. 1 illustrating the inside of the package when a vacuum condition exists therein.

DETAILED DESCRIPTION

While this invention is satisfied by embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Adverting to the drawings, particularly to FIG. 1, there is illustrated one embodiment of an air-evacuated package assembly 10 of the present invention. Package assembly 10 includes an air-impervious package 12 which has been sealed along seal line 14 to enclose the contents within the package. It can be seen in FIG. 1 that package assembly 12 is in a relatively flat condition inasmuch as it has been air-evacuated. This flat condition of the package serves to indicate to the user that vacuum conditions exist inside the package, and will be explained in greater detail hereinafter.

Turning now to FIGS. 2 and 3, package 12, in the embodiment being described, is a container which is sufficiently flexible to expand outwardly to thereby increase the volume of the interior space of the package. While it is preferred that the entire package be made of a flexible material, such as a thin sheet of plastic or coated paper, it is also within the purview of this invention to include packages which may be partly rigid and partly flexible, if desired by the fabricator. It can be seen in the drawings that package 12 includes an access opening 15 communicating with the interior of the package. More than one access opening may be provided, if desired, but this will necessitate a multiplicity of seals thereafter when evacuating the package. Thus, it is preferable to keep the number of access opening seals to a minimum in order to reduce the areas of possible leakage.

Various articles 16 are placed inside package 12 through access opening 15. These articles are usually clean, sterile or perishable articles which, by nature, are best preserved by being in an evacuated environment. Of course, package 12 is sized to be compatible with the size of the articles which are to be placed therein. One or more articles 16 may be placed inside the package, once again depending upon the respective sizes, shapes and volumes of both package 12 and articles 16. In addition to the articles, a compressible member 18 is also placed inside package 12 through access opening 15. Compressible member 18 is illustrated in the embodiment being described as a block of high-density, open cell foam material. This material has the capability of being compressed under the influence of the supporting package structure and pressure less than atmospheric pressure. The open cell nature of the foam material contributes to allow its structure to become compressed under this pressure differential. As seen in FIG. 4, taken in conjunction with FIG. 3, articles 16 and compressible member 18 have been placed inside package 12. Opening 15 has not yet been sealed so that atmospheric pressure conditions exist both inside and outside package 12. Compressible member 18 has sufficient size and structural rigidity when at the atmospheric pressure level to press against the inside wall 19 of the package. Due to its flexible nature, at the atmospheric pressure level, the package expands outwardly to provide a bloated appearance.

Once the package assembly is air-evacuated, it takes on a different structural appearance as illustrated in FIG. 5. Package 12 has its access opening 15 sealed along a closure seal 14 following evacuation of the air inside. This closure seal may be performed by many different techniques in order to provide a sufficient closure to maintain vacuum conditions inside the package. It can be seen that in the vacuum condition, compressible member 18 has been substantially compressed due to the lower pressure inside the package as compared to the pressure outside the package. In this condition, walls 19 of the package, due to their flexible nature, contract inwardly along with the compressed condition of the compressible member. Overall, the air-evacuated package takes on a substantially reduced size as compared to the non-air-evacuated package, as clearly seen when referring to FIGS. 4 and 5.

Should either closure seal 14 or the package material itself fail, rupture or be otherwise defective, the vacuum inside the package will tend to equalize with the higher existing atmospheric pressure outside the package. Once the vacuum condition inside the package is compromised, compressible member 18 is induced back to its originally larger size at normal, atmospheric pressure levels. As this occurs, compressible member 18 once again presses against walls 19 of the package to thereby expand the same outwardly. Therefore, it becomes quite apparent that a certain package does not have the proper vacuum within due to the substantially increased size as compared to properly evacuated packages. This quick and ready visual indicator of proper vacuum conditions is a significant improvement in making this kind of determination over that which has been performed previously.

Although the compressible member as described herein may be made of many different materials, it is preferred that it be a high-density, open cell foam material, such as polyurethane, polyethylene, polyether, and the like. Also, while the compressible member has been illustrated herein as having a block form, other volumetric shapes may also be utilized, such as spheres, cones, and the like. It should be pointed out that there should be no interference between the compressible member and the articles which would prevent the compressible member from expanding outwardly against the package wall if the vacuum condition ceases. In other words, if the articles are either too large or too numerous and provide an obstacle to the expansion of the compressible member, the desired function of the compressible member could be lost. Care should be taken to ensure that placement of the compressible member inside the package allows the flexible walls to be expanded by virtue of growth of the compressible member if the vacuum inside the package ceases.

Thus, the present invention provides a quick and ready visual indicator in the use of air-evacuated, flexible packages with articles therein, as to whether or not there is indeed a vacuum inside. This is a notable improvement in making the determination of vacuum in these kinds of packages.

What is claimed is:

1. An evacuated article-containing package assembly with vacuum integrity indicator means comprising:
   an air-impervious, flexible package having an access for the placement of an article therein;
   an article inside said package;
   a compressible member inside said package being compressible under the influence of pressure less than atmospheric pressure; and
   a closure seal on said package sealing said access after said article and said compressible member are within said package under air-evacuated conditions, said sealed package being air-evacuated, said compressible member adapted to expand against said flexible package to thereby outwardly expand said flexible package if the pressure inside said package should substantially equal the pressure outside said package, said expanded flexible package thereby serving as a visual indicator that there is no vacuum condition inside said package.

2. The package assembly of claim 1 wherein the package is made of flexible plastic.

3. The package assembly of claim 1 wherein the package is made of paper which has been coated to render the same air-impervious.

4. The package assembly of claim 1 wherein the compressible member is a high-density, open cell foam material.

5. The package assembly of claim 4 wherein said foam material is polyurethane.

6. The package assembly of claim 4 wherein said foam material is polyethylene.

7. The package assembly of claim 4 wherein said foam material is polyether.

8. An evacuated article-containing package assembly with vacuum integrity indicator means comprising:
- an air-impervious package having an access opening and at least a flexible portion thereof;
- an article inside said package;
- compressible means inside said package being compressible under the influence of pressure less than atmospheric pressure; and
- sealing means on said package sealing said access opening, said sealed package being air-evacuated, said compressible means adapted to expand against said flexible portion of said package to thereby outwardly expand said flexible portion if the pressure inside said package should substantially equal the pressure outside said package, said expanded flexible portion thereby serving as a visual indicator that there is no vacuum condition inside said package.

9. An evacuated article-containing package assembly with vacuum integrity indicator means comprising:
- an air-impervious flexible paper package having an access for the placement of an article therein;
- an article inside said package;
- a high-density, open cell, compressible foam material inside said package being compressible under the influence of pressure less than atmospheric pressure; and
- a closure seal on said package sealing said access after said article and said compressible material are within said package under air-evacuated conditions, said sealed package being air-evacuated, said compressible material adapted to expand against said flexible package to thereby outwardly expand said flexible package if the pressure inside said package should substantially equal the pressure outside said package, said expanded flexible package thereby serving as a visual indicator that there is no vacuum condition inside said package.

* * * * *